United States Patent [19]

Vigelius et al.

[11] 4,104,380

[45] Aug. 1, 1978

[54] DIBENZYL GLYCOLIC ACID DERIVATIVES

[75] Inventors: Wolf-Dieter Vigelius; Gerhard Satzinger, both of Denzlingen; Manfred Herrmann, St. Peter, all of Germany

[73] Assignee: Warner-Lambert Company, Morris Plains, N.J.

[21] Appl. No.: 777,731

[22] Filed: Mar. 15, 1977

Related U.S. Application Data

[63] Continuation of Ser. No. 696,665, Jun. 16, 1976.

[51] Int. Cl.² .............................................. A61K 31/55
[52] U.S. Cl. ................................ 424/244; 424/248.55; 424/308; 424/274; 424/267

[58] Field of Search .................. 424/244, 248.55, 308, 424/274, 267

[56] References Cited

PUBLICATIONS

LesPanol, et al., CA, vol. 69, 106,476z (1968).
LesPanol, et al., CA, vol. 70, 66,557s (1969).

*Primary Examiner*—Nicholas S. Rizzo
*Attorney, Agent, or Firm*—Albert H. Graddis; Frank S. Chow; George M. Yahwak

[57] ABSTRACT

The present invention is concerned with new dibenzylglycolic acid derivatives and with the preparation thereof. These derivatives show an extraordinary antihypertensive and antisecretory profile.

43 Claims, No Drawings

DIBENZYL GLYCOLIC ACID DERIVATIVES

This is a continuation of application Ser. No. 696,665 filed June 16, 1976.

The new dibenzyl-glycolic acid derivatives according to the present invention are compounds of the general formula:

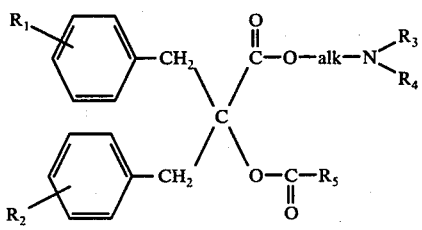

wherein $R_1$ and $R_2$, which may be the same or different, are hydrogen or halogen atoms or alkyl or alkoxy radicals containing up to 3 carbon atoms, $R_3$ and $R_4$, which may be the same or different, are alkyl radicals containing up to 3 carbon atoms or $R_3$ and $R_4$, together with the nitrogen atom to which they are attached, can also form a saturated or unsaturated mono-, bi- or tricyclic ring containing 3 to 17 carbon atoms which, in the ring system, can contain a further imino group or an oxygen atom and which can be substituted by a phenyl or benzyl radical or by one or more alkyl radicals containing up to 4 carbon atoms, $R_5$ is a hydrogen atom or an alkyl or alkoxy radical containing up to 5 carbon atoms or a benzyl radical and alk is a branched or unbranched alkylidene radical containing 2 to 4 carbon atoms; and the quaternary lower alkyl ammonium salts thereof, as well as the pharmacologically compatible salts thereof with inorganic and organic acids.

The halogen atoms in the above-given general formula (I) are fluorine, chlorine or bromine atoms. Chlorine atoms are preferred.

When $R_3$ and $R_4$, together with the nitrogen atom to which they are attached, form a ring, it can be, for example, any one of the following ring systems: azetidine, pyrrolidine, $\Delta^2$-pyrroline, $\Delta^3$-pyrroline, piperidine, piperazine, morpholine, tetrahydropyridine, tetrahydroquenoline, tetrahydroisoquinoline, 2,2,6,6-bis-tetramethylenepyrrolidine, 2,2,6,6-bis-tetramethylenepyrrolidine, 4,4-tetramethylene-piperidine, 4,4-pentamethylene-piperidine, 4,4-hexamethylene-piperidine, hexahydroazepine and 3-aza-bicyclo[3.2.2]nonane. These further can be substituted by a phenyl or benzyl radical or by one or more alkyl radicals containing up to 4 carbon atoms, preferably methyl and/or ethyl radicals.

The substituent $R_5$ is a hydrogen atom or a methyl, ethyl, n-propyl, isopropyl, n-butyl, isobutyl, tert.-butyl, methoxymethyl or benzyl radical.

As branched or unbranched alkylidene radicals, ethylene, trimethylene and propylene radicals are preferred.

Compounds of general formula (I) are preferred in which $R_1$ and $R_2$, which may be the same or different, are hydrogen or chlorine atoms or methyl or methoxy radicals, and $R_3$ and $R_4$, together with the nitrogen atom to which they are attached, form a piperidine, 2,2,6,6-tetramethylpiperidine, hexahydroazepine or morpholine ring, $R_5$ is a methyl, ethyl or benzyl radical and "alk" is an ethylene radical.

Representatives of the new compounds (I) include acetyl-dibenzyl-glycolic acid β-piperidinoethyl ester hydrochloride and acetyl-dibenzyl-glycolic acid β-(2,2,6,6-tetramethylpiperidino)-ethyl ester.

In *Bull. Soc. Pharm. Lille*, 1, 31–41/1968, there are described dibenzyl-glycolic acid derivatives which are not esterified on the hydroxyl group, which derivatives show a spasmolytic action (see Chem. Abs., 69, 10, 6476 z). In addition to the spasmolytic effect, dibenzyl-glycol acid derivatives are also shown to have a hypotensive action (see Bull. Soc. Pharm. Lille, 2, 79–85/1968; Chem. Abs. 70, 66567 s).

We have now found that compounds of general formula (I) are characterized by an extraordinary antihypertensive and anti-secretory action profile. In contradistinction to the hypotensive action appearing in the case of many known substances, i.e. a blood pressure lowering in normotonic animals upon parenteral administration, the new compounds according to the present invention are essentially only effective when high blood pressure is present; the blood pressure can be reduced, not only in the case of oral but also parenteral administration, quickly and longlastingly to a desired normal level and without danger of hypotonia. Some of the new compounds (I) also exhibit anti-secretory action; they are especially suited for the treatment of hyperacidity.

Compounds according to the present invention can be prepared by reacting, in any desired sequence, a compound of the general formula:

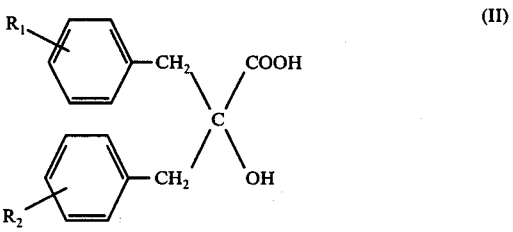

wherein $R_1$ and $R_2$ have the same meanings as above, or a reactive derivative thereof, with (a) a compound of the general formula:

in which $R_5$ has the same meaning as above or with a reactive derivative thereof, and with (b) a compound of the general formula:

or with a reactive derivative thereof. The compound (I) thus obtained is, if desired, subsequently converted into a compatible quaternary lower alkyl ammonium salt or a salt of an organic or inorganic acid.

The compound of general formula (II) in which $R_1$ and $R_2$ are both hydrogen atoms is known [oxatolylic acid (see Beilstein, 10, H 350)]. A process for the preparation of oxatolylic acid is described in Chem. Berichte, 13, p. 2220, and also in Helv. Chim. Acta, 28, 744–746/1945. These processes can also be used for the preparation of phenyl-substituted oxatolylic acid derivatives. Oxatolylic acid and its phenyl-substituted derivatives can be prepared by the reaction of diethyl oxalate with optionally phenyl-substituted benzyl magnesium halides according to the Grignard method.

Since, in the case of the reaction of compounds (II) with compounds (III) and (IV), esterification reactions take place, as reactive derivatives there are to be understood those compounds which are known to favor the formation of esters. In the case of such esterification reactions, there can be used reactive acid derivatives such as acid halides, especially acid chlorides, acid anhydrides and acid imidazolides. As reactive derivatives of the alcoholic compounds of general formula (IV), there are alkyl halides, especially the chlorides and bromides, as well as reactive esters, such as the tosylates or brosylates.

It is also possible to prepare an alkali metal, alkaline earth metal, silver or mercury salt of a compound (II) and then to react this with a compound of the general formula:

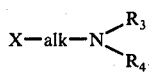 (V)

wherein $R_3$ and $R_4$ and alk have the same meanings as above and X is a halogen atom or a reactive ester group. (Compound (V) is a reactive derivative of the alcohol (IV)), followed by reaction with an acid halide of general formula (III).

Furthermore, it is possible to react a compound of general formula (II) with an anhydride or halide of an acid of the general formula (III) and subsequently to convert the carboxyl group of the compound (II) into an active acid halide group which can be reacted directly with the free hydroxyl group of the compounds (IV).

In principle, it is expedient first to esterify the hydroxyl group of the compounds (II) since, under the esterification conditions for the carboxyl group, this is easily split off as a free tertiary hydroxyl group, which can lead to undesirable side reactions.

In the case of the reaction of acid halides with alcohols, for the removal of the hydrogen halide split off, it is preferable to add a tertiary amine, such as pyridine or triethylamine. The esterification reaction can also be accelerated by the azeotropic removal of water using an entraining mixture such as benzene/alcohol.

The alkali metal salts of the compounds (II) preferred for the reaction with the alkyl halides are prepared by mixing an alcoholic solution of the compounds (II) with an equimolar amount of an alkali metal alcoholate, especially a sodium alcoholate. In this case, it is also possible to work in a solvent mixture with benzene. The salt obtained can be further reacted, if a compound of general formula (V) is slowly added. The salts formed can, after solvent evaporation, be precipitated by the addition of ether.

The compounds (III) can be converted in conventional manner into acid halides, as with acid halides of phosphorus or sulphur. This also applies to compounds of general formula (II), after esterification of the free hydroxyl group.

The reaction of compounds of general formula (II) with compounds of general formula (V) can either take place directly or first be carried out in a reaction with a bromoalkyl chloride, the bromine atom thereby reacting first. The intermediate product obtained can subsequently be converted to the end product by reaction with an amine of general formula:

wherein $R_3$ and $R_4$ have the same meanings as above.

The quaternary ammonium salts of compounds of general formula (I) can be prepared in the usual manner by reacting the free base with an alkyl halide. As solvent for the quaternisation, there can be used ethanol or nitromethane.

The salts of the free amines of general formula (I) can be prepared by reaction with equivalent amounts of inorganic or organic acid solutions. Thus, an anhydrous acid component, such as hydrogen chloride, is passed into or added to an appropriate solution of the base. The solvent for this purpose may be ethyl acetate, ether or methanol.

As pharmacologically compatible salts, there may be mentioned, for example, those with the following acids: hydrochloric acid, hydrobromic acid, sulphuric acid, benzene-sulphonic acid, naphthalene-1,5-disulphonic acid, acetic acid, oxalic acid, salicylic acid, succinic acid, malic acid and citric acid.

The compounds of general formula (I) as well as their pharmacologically compatible quaternary lower alkyl ammonium salts and salts with inorganic and organic acids can be administered enterally or parenterally in admixture with a liquid or solid pharmaceutical diluent or carrier. As injection medium, it is preferred to use water which contains the conventional additives for injection solutions, for example, stabilizing agents, solubilizing agents and buffers, for example, ethanol, complex-forming agents (as ethylene-diamine-tetraacetic acid and the non-toxic salts thereof), tartrate and citrate buffers and high molecular weight polymers (for example liquid polyethylene oxide) for viscosity regulation. Examples of solid carrier materials include starch, lactose, mannitor, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Oral forms of administration can also contain flavoring and/or sweetening agents.

The dosage of the compounds according to the present invention depends upon the nature and severity of the disease to be treated. In the case of hypertonias, oral administration is preferred. The individual dose should be about 20–500 mg. and the subcutaneously or intravenously administered individual dose should be about 2–50 mg.

In the case of gastric diseases, the anti-secretory active oral individual dose is between 20 and 500 mg. Parenteral forms of administration are less suitable in the case of this indication.

The following Examples are given for the purpose of illustrating the present invention.

EXAMPLE 1

Acetyl-dibenzyl-glycolic acid β-piperidinoethyl ester hydrochloride 120.5 g. (0.47 mol) dibenzylglycolic acid and 50.5 g. (0.5 mol) triethylamine are dissolved in 2 liters of crystallized benzene, 39.7 g. (0.5 mol) (i.e. 36.1 ml.), acetyl chloride in 100 ml. crystallized benzene are added dropwise, while stirring and boiling, (in the course of 1 hour)

and the reaction mixture then boiled for 16 hours. After cooling, the precipitated triethylamine hydrochloride is filtered off, the filtrate evaporated, and the syrupy residue is crystallized by vigorously stirring it in 600 ml. of a mixture of diethyl ether/benzine (1:5). The product is filtered off with suction, washed with 250 ml. petroleum ether, and dried. There is obtained 99 g. (70.6% of theory) acetyl-dibenzyl-glycolic acid; m.p. 102°–103° C.

The acetyl-dibenzyl-glycolic acid thus obtained is dissolved in 200 ml. ethanol, added to a solution of 7.6 g. (0.33 g. atom) sodium in 200 ml. ethanol and, while stirring at boiling temperature, mixed dropwise with a 50% benzene solution of 97.4 g. (0.33 mol) N-β-chloroethylpiperidine; the reaction mixture is then boiled for four hours. After cooling, the precipitated sodium chloride is filtered off, the filtrate evaporated, and the residue dissolved in 500 ml. ether, filtered and mixed with 250 ml. hydrogen chloride-saturated ethyl acetate for the complete precipitation of the salt. The hydrochloride is filtered off with suction and crystallized from 5 liters of ethyl acetate. There is obtained 100 g. (68% of theory) acetyl-dibenzyl-glycolic acid β-piperidinoethyl ester hydrochloride; m.p. 174° C.

The dibenzyl-glycolic acid used as starting material is prepared in the following manner:

75 g. (3.2 g. atom) magnesium is reacted by Grignard's method with 380 g. (3 mol) benzyl chloride in 600 ml. dry ether and then boiled for 30 minutes. While cooling externally with ice water, a solution of 146 g. (1mol) diethyl oxalate in 1.5 liters dry ether is added dropwise, while stirring. The reaction mixture is then boiled under reflux for 16 hours. While cooling externally with ice, 1 liter 4N hydrochloric acid is carefully added. The separated aqueous phase is extracted with 1 liter ether and the combined ether phases are shaken out several times with a total of 1 liter saturated potassium bicarbonate solution, dried and evaporated. The residue is boiled for 2 hours in 2.5 liters 10% methanolic potassium hydroxide solution and then evaporated. The residue is dissolved in 3 liters water, extracted twice with 500 ml. amounts of ether and strongly acidified with concentrated hydrochloric acid. The precipitated dibenzyl-glycolic acid is filtered off with suction, washed with 300 ml. benzene and the residue boiled in 2.5 liters benzene (using a water separator) until no more water passes over. The product which crystallizes upon cooling is filtered off with suction and dried. There is obtained 120.5 g. (47% of theory) dibenzyl-glycolic acid; m.p. 156° C.

The N-β-chloroethyl-piperidine used as starting material is prepared in the following manner:

92.1 g. (0.5 mol) Nβ-chloroethyl-piperidine hydrochloride is dissolved in 100 ml. water, rendered alkaline with 10N aqueous sodium hydroxide solution and extracted three times with a total of 500 ml. ether. The ethereal phase is dried, evaporated in a vacuum at 25° C. and the residue fractionated. There is obtained 59 g. (80% of theory) N-β-chloroethyl-piperidine; b.p. 70° C./12 mm.Hg. The distillate must be immediately diluted with an equal weight of benzene and stored at −15° C.

EXAMPLE 2

Acetyl-dibenzyl-glycolic acid β-(2,2,6,6-tetramethyl-piperidino)ethyl ester 3.1 g. (0.134 g. atom) sodium is dissolved in 150 ml. ethanol. To this solution is added 40 g. (0.134 mol) acetyl-dibenzyl-glycolic acid in 150 ml. ethanol and the reaction mixture heated to the boil. Subsequently, 27.5 g. (0.134 mol) 1-β-chloroethyl-2,2,6,6-tetramethyl-piperidine in 27.5 g. benzene is added dropwise and the reaction mixture boiled for 16 hours. After cooling, precipitated sodium chloride is filtered and the filtrate evaporated. The residue is dissolved in 1 liter ether, filtered, evaporated and the oily residue brought to crystallization in 100 ml. benzene, filtered and again crystallized from 100 ml. benzene. There is obtained 34 g. (54.5% of theory) acetyl-dibenzyl-glycolic acid β-(2,2,6,6-tetramethylpiperidino)-ethyl ester; m.p. 82.1° C.

The 1-(β-chloroethyl)-2,2,6,6-tetramethyl-piperidine used as starting material is prepared in the following manner:

56 g. (0.4 mol) 2,2,6,6-tetramethyl-piperidine, 20 g. (0.46 mol) ethylene oxide and 1 ml concentrated hydrochloric acid are dissolved in 100 ml. methanol (while cooling with ice) and heated in a glass autoclave for 4 hours at 100° C. After cooling, the reaction mixture is evaporated. There is obtained 60 g. 1-(β-hydroxy-ethyl)-2,2,6,6-tetramethyl-piperidine; m.p. 96° – 97° C.

The product obtained is dissolved in 150 ml. benzene and (while cooling with ice) a mixture of 75 ml. thionyl chloride and 150 ml. benzene is added dropwise. Thereafter, the reaction mixture is boiled for 3 hours and, after cooling, the hydrochloride is filtered off with suction. There is thus obtained 60 g. 1-(β-chloro-ethyl)-2,2,6,6-tetramethyl-piperidine hydrochloride (m.p. 210°–212° C.) which is converted in the usual manner, using an aqueous solution of sodium hydroxide, into the free base; b.p. 111° C (cf. R. B. Moffett and B. D. Aspergren, J.A.C.S., 82, 1612/1960).

In an analogous manner, there is obtained the following compounds by the reaction of the sodium salt of acetyl-dibenzyl-glycolic acid with:

A. β-dimethylaminoethyl chloride;
   acetyl-dibenzyl-glycolic acid β-dimethylaminoethyl ester, which, after reaction with oxalic acid, is isolated as the oxalate; m.p. 144°–145° C.;
B. β-diethylaminoethyl chloride;
   acetyl-dibenzyl-glycolic acid β-diethylaminoethyl ester, which, after reaction with oxalic acid, is isolated as the oxalate; m.p. 136° C.;
C. β-dimethylaminopropyl chloride:
   acetyl-dibenzyl-glycolic acid β-dimethylaminopropyl ester, which, after reaction with oxalic acid, is isolated as the oxalate; m.p. 154°–155° C.;
D. γ-dimethylaminopropyl chloride:
   acetyl-dibenzyl-glycolic acid γ-dimethylaminopropyl ester, which, after reaction with oxalic acid, is isolated as the oxalate; m.p. 125°–127° C.;
E. β-pyrrolidinoethyl chloride:
   acetyl-dibenzyl-glycolic acid β-pyrrolidinoethyl ester, which, after reaction with oxalic acid, is isolated as the oxalate; m.p. 180°–180.5° C.
F. β-morpholinoethyl chloride:
   acetyl-dibenzyl-glycolic acid β-morpholinoethyl ester, which, after reaction with oxalic acid, is isolated as the oxalate; m.p. 112.5°–113° C.;
G. 1-piperidino-2-chloropropane:
   acetyl-dibenzyl-glycolic acid β-piperidino-isopropyl ester, which, after reaction with naphthalene-1,5-disulphonic acid, is isolated as the heminaphthalene-1,5-disulphonate; m.p. 190.8° C.;
H. 2-piperidino-1-chloropropane:
   acetyl-dibenzyl-glycolic acid β-piperidinopropyl ester, which, after reaction with napthalene-1,5- disulphonic acid, is isolated as the hemi-naphthalene-1,5-disulphonate; m.p. 189.2° C.

I. γ-piperidino-propyl chloride:
acetyl-dibenzyl-glycolic acid γ-piperidinopropyl ester, which, after reaction with oxalic acid, is isolated as the oxalate; m.p. 156° C.;

J. β-(2-methyl-piperidino)-ethyl chloride:
acetyl-dibenzyl-glycolic acid β-(2-methyl-piperidino)-ethyl ester, which, after reaction with oxalic acid, is isolated as the oxalate; m.p. 117° C.;

β-(3-methyl-piperidino)-ethyl chloride:
acetyl-dibenzyl-glycolic acid β-(3-methyl-piperidino)-ethyl ester, which, after reaction with oxalic acid, is isolated as the oxalate; m.p. 104°-105° C.;

K. β-(4-methyl-piperidino)-ethyl chloride:
acetyl-dibenzyl-glycolic acid β-(4-methyl-piperidino)-ethyl ester, which, after reaction with oxalic acid, is isolated as the oxalate; m.p. 158° C.

The β-(4-methyl-piperidino)-ethyl chloride used as starting material is prepared in the following manner:

To 138.9 g. (1.4 mol) 4-methyl-piperidine is added dropwise, while stirring 56.3 g. (0.7 mol) (47 ml.) ethylene chlorohydrin. After boiling the reaction mixture for 3 hours, it is cooled, stirred up several times with a total of 1.5 liters ether; precipitated 4-methyl-piperidine hydrochloride is filtered off and the residue evaporated. The residue obtained is then fractionated in a vacuum. There is obtained 91.7 g. (0.63 mol) 4-methylpiperidinoethanol. This is dissolved in 500 ml. anhydrous benzene and, while stirring, so mixed with a solution of 151.2 g. (1.26 mol) thionyl chloride in 100 ml. anhydrous benzene that the temperature of the mixture remains between 25° and 30° C. After boiling for a further 30 minutes, the hydrochloride (m.p. 142°-144° C.) is filtered off with suction and washed out with ether. Yield 123 g. (98.5% of theory).

40 g. (0.2 mol) β-4-methyl-piperidinoethyl chloride hydrochloride are dissolved in 100 ml. water, rendered alkaline with an aqueous solution of sodium hydroxide and extracted several times with a total of 1 liter ether. The ethereal phase is dried and evaporated and the residue obtained then distilled. There are obtained 26.7 g. (83% of theory) β-4-methyl-piperidinoethyl chloride; b.p. 75°-76° C./12 mm.Hg., L. β-(2,6-dimethyl-piperidino)-ethyl chloride:
acetyl-dibenzyl-glycolic acid β-(2,6-dimethyl-piperidino)-ethyl ester, which, after reaction with oxalic acid, is isolated as the oxalate; m.p. 115°-116° C.

EXAMPLE 3

Acetyl-dibenzyl-glycolic-acid β-(4-phenyl-piperidino)-ethyl ester oxalate 13.5 g. (0.067 mol) β-(4-phenyl-piperidino)-ethyl chloride in 20 ml. ethanol is added dropwise to a solution of 20 g. (0.067 mol) acetyl-dibenzyl-glycolic acid sodium salt in 140 ml. ethanol. The reaction mixture is boiled for 16 hours, filtered and the filtrate evaporated. The residue is dissolved in 200 ml. ether, the oxalate is precipitated out by the addition of a dry saturated ethereal solution of oxalic acid, and the oxalate crystallized twice from 500 ml. amounts of ethanol. There is obtained 22.6 g. (60% of theory) acetyl-dibenzyl-glycolic acid β-(4-phenyl-piperidino)-ethyl ester oxalate; m.p. 146° C.

The β-(4-phenyl-piperidino)-ethyl chloride used as starting material is prepared in the following manner:

75 g. (0.46 mol) β-4-phenylpiperidine is heated with 38 g. (0.46 mol) 2-chloroethanol for 5 hours at about 120° C. After cooling, the reaction mixture is dissolved in 500 ml. water, rendered alkaline with potassium carbonate, extracted with 1 liter ether, dried, evaporated and the residue distilled in a high vacuum. There is obtained 55 g. (61% of theory) β-(4-phenyl-piperidino)-ethanol (b.p. 155° C./0.2 mm.Hg.), which is dissolved in 500 ml. chloroform. The corresponding hydrochloride is then precipitated out by the addition of dry hydrogen chloride. 50 ml. thionyl chloride is added and the reaction mixture heated under reflux for 5 hours and cooled. The precipitated product is filtered off, dissolved in 300 ml. water and rendered alkaline with 10N aqueous sodium hydroxide solution. The precipitated base is extracted with 500 ml. ether, dried and evaporated. There is obtained 45 g. (75% of theory) β-(4-phenyl-piperidino)-ethyl chloride.

EXAMPLE 4

Acetyl-dibenzyl-glycolic acid β-(4,4-pentamethylene-piperidino)-ethyl ester oxalate.

2.02 g. (0.088 g. atom) sodium is dissolved in 50 ml. absolute ethanol and 26.3 g. (0.088 mol) acetyl-dibenzyl-glycolic acid, dissolved in 50 ml. absolute ethanol, added thereto and, while stirring and boiling, a 50% benzene solution, containing 19 g. (0.088 mol) β-(4,4-pentamethylene-piperidino)-ethyl chloride is added dropwise. After boiling for 4 hours, the reaction mixture is cooled, the precipitated sodium chloride filtered off, the filtrate evaporated, and the residue taken up in 500 ml. dry ether, filtered and mixed with a saturated, dried ethereal solution of oxalic acid until precipitation is complete. The oxalate is filtered and crystallized twice with 600 ml. amounts of ethanol/ethyl acetate (1:5). There is obtained 20 g. (40% of theory) acetyl-dibenzyl-glycolic acid β-(4,4-pentamethylene-piperidino)-ethyl ester oxalate; m.p. 163.3° C.

The β-(4,4-pentamethylene-piperidino)-ethyl chloride used as starting material is prepared in the following manner:

50 g. (0.25 mol) cyclohexane-diacetic acid, 15 g. (0.25 mol) aminoethanol and a spatula tip of piperidine acetate is boiled for about 8 hours in 500 ml xylene, under a water separator, until 9 ml. of water have separated. After evaporation of the solvent, the residue is fractionated in a high vacuum. There is obtained 45 g. (70% of theory) β,β-pentamethylene-N-(β-hydroxyethyl)-glutarimide; b.p. 162° - 165° C./0.5 mm.Hg.

To a solution of 52 g. (0.23 mol) β,β-pentamethylene-N-(β-hydroxyethyl)-glutarimide in 500 ml. anhydrous benzene, there is added dropwise a mixture of 240 ml. (0.83 mol) of a 70% solution of sodium dihydro-bis-(2-methoxyethoxy) aluminate in benzene with 150 ml. absolute benzene while stirring and under an atmosphere of nitrogen, so that the internal temperature of the reaction mixture does not exceed 30° C. After boiling the reaction mixture for 24 hours under an atmosphere of nitrogen, it is cooled with ice, carefully mixed with about 200 ml. water, filtered free of aluminum hydroxide, the filtrate dried and evaporated and the residue fractionated in a vacuum. There is obtained 29.7 g. (65% of theory) β-(4,4-pentamethylene-piperidino)- ethanol is dissolved in 100 ml. chloroform, saturated with hydrogen chloride, 90 ml. thionyl chloride added thereto and the reaction mixture then boiled for 3 hours. After evaporating about two thirds of the reaction mixture, 200 ml. carbon tetrachloride is added. The mixture is subsequently stirred (30 minutes) and about two thirds of the solvent is distilled off. This is repeated, the solvent is filtered off and the residue is stirred for 1 hour in 200 ml. ether. The crude hydrochloride (23 g.) (m.p. 262.5° C.) is suspended in 100 ml. water, 0.1N aqueous sodium hydroxide solution is added until strongly alkaline and the mixture is extracted several times with a total of 500 ml. ether. After drying and evaporating the combined ethereal extracts, there is obtained 19 g. (19% of theory) β-(4,4-pentamethylene-piperidino)-ethyl chloride. For storing the base, it can be diluted with an equal amount by weight of benzene and kept at −15° C.

EXAMPLE 5

Acetyl-dibenzyl-glycolic acid β-piperidinoethyl ester methobromide 9.5 g. (0.02 mol) acetyl-dibenzyl-glycolic acid β-piperidino ethyl ester (see Example 1), 20 g. (0.2 mol) methyl bromide and a spatula tip of potassium iodide is left to stand for 20 hours in 50 ml. nitromethane. After evaporation in a vacuum, the residue is recrystallized from 250 ml. of a mixture of ethanol/ethyl acetate (1:9). There is obtained 7.4 g. (74% of theory) acetyl-dibenzyl-glycolic acid β-piperidinoethyl ester methobromide; m.p. 206°–207° C.

EXAMPLE 6

Acetyl-dibenzyl-glycolic acid β-hexamethyleneiminoethyl ester hydrochloride

In a manner analogous to that described in Example 1, by the reaction of acetyl-dibenzyl-glycolic acid with N-β-chloroethyl-hexamethyleneimine, there is obtained acetyl-dibenzyl-glycolic acid β-hexamethyleneiminoethyl ester hydrochloride; m.p. 153°–154° C.

EXAMPLE 7

Acetyl-dibenzyl-glycolic acid β-hexamethyleneiminoethyl ester methobromide

In a manner analogous to that described in Example 5, by the reaction of the free base described in Example 6 with methyl bromide, in nitromethane, there is obtained acetyl-dibenzyl-glycolic acid β-hexamethyleneiminoethyl ester methobromide; m.p. 198.5° C.

EXAMPLE 8

Propionyl-dibenzyl-glycolic acid β-dimethylaminoethyl ester oxalate 1.5 g. (0.065 g. atom) sodium is dissolved in 50 ml. absolute ethanol, mixed with 20.4 g. (0.065 mol) propionyl-dibenzyl-glycolic acid in 50 ml. absolute ethanol and 7.03 g. (0.065 mol) β-dimethylaminoethyl chloride in benzene solution added. After boiling for about 8 hours, the reaction mixture is cooled, precipitated sodium chloride is filtered off and the filtrate is evaporated. The residue is taken up in ether and, after treatment with charcoal, mixed with a saturated, dried, ethereal solution of oxalic acid until precipitation is complete. The oxalate is filtered off and crystallized twice from 250 ml. amounts of isopropanol. There is obtained 8.8 g. (28.5% of theory) propionyl-dibenzyl-glycolic acid β-dimethylaminoethyl ester oxalate; m.p. 137°–138° C.

The propionyl-dibenzyl-glycolic acid used as starting material is prepared in the following manner:

51.2 g. (0.2 mol) dibenzyl-glycolic acid is boiled for 4 hours with 52 g. (0.4 mol) propionic acid anhydride. After distilling off on a steambath in a vacuum excess propionic acid anhydride and propionic acid formed, the residue is dissolved in 50 ml. alcohol and poured into 800 ml. dilute ammonia solution (1:1), while stirring. After standing for about 2 hours, the mixture is filtered off and the filtrate acidified with hydrochloric acid, while cooling. The oily acid which precipitates out is extracted with a total of about 500 ml. ether and the ether then evaporated. The oily product (24 g.; 38.5% of theory) is used for the further reaction. However, by repeated treatment with hexane, the oily propionyl-dibenzyl-glycolic acid can be crystallized; m.p. about 80° C.

The following compounds are obtained in an analogous manner:

propionyl-dibenzyl-glycolic acid β-diethylaminoethyl ester oxalate; m.p. 123.5° – 125° C.;

propionyl-dibenzyl-glycolic acid β-pyrrolidinoethyl ester oxalate; m.p. 181°–182° C.;

propionyl-dibenzyl-glycolic acid β-piperidinoethyl ester oxalate; m.p. 163.5° – 164.5° C.

propionyl-dibenzyl-glycolic acid β-morpholinoethyl ester oxalate; m.p. 134° – 135° C.;

propionyl-dibenzyl-glycolic acid β-dimethylaminopropyl ester oxalate; m.p. 148° – 149° C.

EXAMPLE 9

Isobutyryl-dibenzyl-glycolic acid β-piperidinoethyl ester hydrochloride 30 g. (0.095 mol) isobutyryl-dibenzyl-glycolic acid is dissolved in 150 ml. ethanol and added to a solution of 2.3 g. (0.1 g. atom) sodium in 150 ml. ethanol. Subsequently, 13 g. (0.095 mol) β-chloroethyl-piperidine in 13 g. benzene is added and the reaction mixture boiled for 8 hours. After cooling, precipitated sodium chloride is filtered off, the filtrate is evaporated and the residue is taken up in 200 ml. ethyl acetate, mixed with hydrogen chloride-saturated ethyl acetate until precipitation of the salt is complete and then filtered and crystallized three times from 250 ml. amounts of a mixture of acetone/ethyl acetate (1:5). There is obtained 11.6 g. (24% theory) isobutyryl-dibenzyl-glycolic acid β-piperidinoethyl ester hydrochloride; m.p. 139° – 140° C.

The isobutyryl-dibenzyl-glycolic acid used as starting material is prepared in the following manner:

25.6 g. (0.1 mol) dibenzyl-glycolic acid is dissolved in 8 g. (0.1 mol) pyridine and 200 ml. anhydrous benzene, while boiling and 10 g. (0.1 mol) isobutyric acid chloride in 30 ml. anhydrous benzene added thereto dropwise. After boiling the reaction mixture for 10 hours, precipitated pyridine hydrochloride is filtered off, the filtrate is evaporated and the crude residue is further worked up. There is obtained 30 g. (80% of theory) isobutyryl-dibenzyl-glycolic acid; m.p. 75° C.

In an analogous manner, by the reaction of dibenzyl-glycolic acid with (a) pivaloyl chloride
(b) β-piperidinoethyl chloride there is obtained pivaloyl-dibenzyl-glycolic acid β-piperidino-ethyl ester oxalate; m.p. 158° – 159° C.;

(a) methoxyacetyl chloride (b) β-piperidinoethyl chloride
there is obtained methoxyacetyl-dibenzyl-glycolic acid β-piperidinoethyl ester hydrochloride; m.p. 95° – 96° C.;

(a) phenylacetyl chloride
(b) β-piperidinoethyl chloride
there is obtained phenylacetyl-dibenzyl-glycolic acid (β-piperidinoethyl) ester hydrochloride; m.p. 129° – 130° C.

EXAMPLE 10

Acetyl-o,o'-dichlorodibenzyl-glycolic acid (β-piperidino-ethyl)-ester hydrochloride To a solution of 25 g. (0.07 mol) acetyl-o,o'-dichlorodibenzylglycolic acid in 70 ml. ethanol, there is added a solution of 1.7 g. (0.7 g. atom) sodium in 70 ml. ethanol. The reaction mixture is heated to the boil and slowly mixed with a solution of 10.5 g. β-piperidinoethyl chloride in 10.5 g. benzene. The mixture is boiled for 16 hours, evaporated and the residue dissolved in 500 ml. ether. The salt is precipitated out by the addition of hydrogen chloride-saturated ethyl acetate, filtered off and recrystallized twice from 1.5 litre amounts of ethyl acetate. There is obtained 11.5 g. (32% of theory) acetyl-o,o'-dichlorodibenzyl-glycolic acid (β-piperidinoethyl)-ester hydrochloride; m.p. 180.9° C.

The acetyl-o,o'-dichlorodibenzyl-glycolic acid used as starting material is prepared in the following manner:

146 g. (1 mol) oxalic acid diethyl ester, dissolved in 1.2 liters dry ether is slowly added dropwise to a Grignard solution prepared from 73 g. (3 g. atom) magnesium and 480 g. (3 mol) o-chlorobenzyl chloride in 600 ml. dry ether and the reaction mixture boiled for 16 hours. While cooling with ice, the mixture is decomposed with 1 liter 10% hydrochloric acid and the ethereal phase is separated off, washed with 1 liter 10% sodium bicarbonate solution, evaporated and the residue boiled for 2 hours in 2.5 liters 10% methanolic potassium hydroxide solution. After evaporating, the residue obtained is dissolved in 3 liters water, extracted twice with 500 ml. amounts of ether, strongly acidified with concentrated hydrochloric acid and the acid then filtered off and crystallized from 2 liters toluene. There is obtained 130 g. (40% of theory) o,o'-dichlorodibenzyl-glycolic acid; m.p. 165°-166° C.

110 g. (0.3 mol) of the o,o'-dichlorodibenzyl-glycolic acid so obtained and 33 g. (0.33 mol) triethylamine are mixed dropwise, in 2 liters dry boiling benzene, with 24 ml. (0.33 mol) acetyl chloride, boiled for 16 hours, cooled, triethylamine hydrochloride filtered off, the filtrate evaporated and the residue stirred with 500 ml. of a mixture of ether/benzene, filtered and dried. There is obtained 90 g. (81.7% of theory) acetyl-o,o'-dichlorodibenzyl-glycolic acid; m.p. 165° C.

In an analogous manner to Example 10, acetyl-o,o'-dichlorodibenzylglycolic acid β-(2,2,6,6-tetramethylpiperidino)-ethyl ester hydrochloride (m.p. 181.7° C.) is obtained by the reaction of acetyl-o,o'-dichlorodibenzylglycolic acid with β-(2,2,6,6-tetramethylpiperidino)-ethyl chloride.

Similarly, acetyl-o,o'-dichlorodibenzyl-glycolic acid β-hexamethyleneiminoethyl ester hydrochloride (m.p. 135.8° C.) is obtained by the reaction of acetyl-o,o'-dichlorodibenzyl-glycolic acid and β-hexamethyleneiminoethyl chloride.

The following compounds are obtained in an analogous manner:

acetyl-di-(o-xylyl)-glycolic acid β-piperidinoethyl ester hydrochloride; m.p. 184.4° C.;

acetyl-di-(o-xylyl)-glycolic acid β-(2,2,6,6-tetramethylpiperidino)-ethyl ester hydrochloride; by the reaction of acetyl-di-(o-xylyl)-glycolic acid with β-2,2,6,6-tetramethylpiperidinoethyl chloride;

acetyl-di-(m-xylyl)-glycolic acid β-piperidinoethyl ester by the reaction of acetyl-di-(m-xylyl)-glycolic acid with β-piperidinoethyl chloride;

acetyl-di-(m-xylyl)-glycolic acid β-(2,2,6,6-tetramethylpiperidino)-ethyl ester by the reaction of acetyl-di-(m-xylyl)-glycolic acid with β-(2,2,6,6-tetramethylpiperidino)-ethyl chloride;

acetyl-di-(p-xylyl)-glycolic acid β-pipeidinoethyl ester by the reaction of acetyl-di-(p-xylyl)-glycolic acid with β-piperidinoethyl chloride;

acetyl-di-(p-xylyl)-glycolic acid β-(2,2,6,6-tetramethylpiperidino)-ethyl ester by the reaction of acetyl-di-(p-xylyl)-glycolic acid with β-(2,2,6,6-tetramethylpiperidino)-ethyl chloride.

The di-xylyl-glycolic acids used as starting materials are prepared by the Grignard reaction of diethyl oxalate with xylyl-magnesium chlorides. As intermediate products, there are obtained di-(o-xylyl)-glycolic acid (m.p. 99.2° C.), acetyl-di-(o-xylyl)-glycolic acid (m.p. 106° – 107° C.), di-(p-xylyl)-glycolic acid (m.p. 136° – 137° C.), acetyl-di-(p-xylyl)-glycolic acid (glassy, non-crystalline), as well as the m-analogues.

Similarly, the following compounds can also be prepared:

acetyl-p,p'-dimethoxydibenzyl-glycolic acid β-piperidinoethyl ester by the reaction of acetyl-p,p'-dimethoxydibenzylglycolic acid with β-piperidinoethyl chloride;

acetyl-p,p'-dimethoxydibenzyl-glycolic acid β-(2,2,6,6-tetramethylpiperidino)-ethyl ester by the reaction of acetyl-p,p'-dimethoxydibenzyl-glycolic acid with β-(2,2,6,6-tetramethylpiperidino)-ethyl chloride;

acetyl-dibenzyl-glycolic acid β-(4-methylpiperazino-1)-ethyl ester by the reaction of acetyl-dibenzyl-glycolic acid with β-(4-methylpiperazino-1)-ethyl chloride;

acetyl-dibenzyl-glycolic acid β-(4-benzylpiperazino-1)-ethyl ester by the reaction of acetyl-dibenzyl-glycolic acid with β-(4-benzylpiperazino-1)-ethyl chloride;

acetyl-dibenzyl-glycolic acid β-(4-phenyl-piperazino-1)-ethyl ester by the reaction of acetyl-dibenzyl-glycolic acid with β-(4-phenyl-piperazino-1)-ethyl chloride;

acetyl-p,p'-diethoxydibenzyl-glycolic acid β-piperidinoethyl ester by the reaction of acetyl-p,p'-diethoxydibenzylglycolic acid with β-piperidinoethyl chloride;

acetyl-dibenzyl-glycolic acid β-(1,2,5,6-tetrahydro-γ-picoloylo)-ethyl ester by the reaction of acetyl-dibenzylglycolic acid with β-(1,2,5,6-tetrahydro-δ-picolylo)-ethyl chloride;

acetyl-dibenzyl-glycolic acid β-(1,2,3,4-tetrahydroquinolino)-ethyl ester by the reaction of acetyl-dibenzylglycolic acid with β-(1,2,3,4-tetrahydroquinolino)-ethyl chloride;

acetyl-dibenzyl-glycolic acid β-(2,2,4,4-tetramethylazetidino)-ethyl ester by the reaction of acetyl-dibenzylglycolic acid with β-(2,2,4,4-tetramethylazetidino)-ethyl chloride;

acetyl-dibenzyl-glycolic acid β-(2,2,5,5-tetramethylpyrrolidino)-ethyl ester by the reaction of acetyl-dibenzylglycolic acid with β-(2,2,5,5-tetramethylpyrrolidino)-ethyl chloride;

acetyl-dibenzyl-glycolic acid β-(2,2,5,5-tetramethyl-Δ³,⁴-pyrrolino)-ethyl ester by the reaction of acetyl-dibenzylglycolic acid with β-(2,2,5,5-tetramethyl-Δ³,⁴-pyrrolino)-ethyl chloride;

acetyl-dibenzyl-glycolic acid β-(4,4-dimethyl-piperidino)-ethyl ester by the reaction of acetyl-dibenzyl-glycolic acid with β-(4,4-dimethylpiperidino)-ethyl chloride;

acetyl-dibenzyl-glycolic acid β-(3,3,5,5-tetramethyl-piperidino)-ethyl ester by the reaction of acetyl-dibenzylglycolic acid with β-(3,3,5,5-tetramethyl-piperidono)-ethyl chloride;

acetyl-dibenzyl-glycolic acid β-(2,2,6,6-tetraethyl-piperidino)-ethyl ester by the reaction of acetyl-dibenzylglycolic acid with β-(2,2,6,6-tetraethylpiperidino)-ethyl chloride; acetyl-dibenzyl-glycolic acid β-(2,2,4,4-bis-tetramethylenepiperidino)-ethyl ester by the reaction of acetyldibenzyl-glycolic acid with β-(2,2,4,4-bis-tetramethylenepiperidino)-ethyl chloride;

acetyl-dibenzyl-glycolic acid β-(2,2,4,4-bis-pentamethylenepiperidino)-ethyl ester by the reaction of acetyl-dibenzyl-glycolic acid with β-(2,2,4,4-bis-pentamethylenepiperidino)-ethyl chloride;

acetyl-dibenzyl-glycolic acid β-(3-aza-bicyclo[3.2.2-]nonano)-ethyl ester by the reaction of acetyl-dibenzyl-glycolic acid with β-(3-aza-bicyclo[3.2.2]nonano)-ethyl chloride;

acetyl-dibenzyl-glycolic acid β-(4,4-tetramethylenepiperidino)-ethyl ester by the reaction of acetyl-dibenzyl-glycolic acid with β-(4,4-tetramethylene-piperidino)-ethyl chloride;

acetyl-dibenzyl-glycolic acid β-(4,4-hexamethylenepiperidino)-ethyl ester by the reaction of acetyl-dibenzyl-glycolic acid with β-(4,4-hexamethylene-piperidino)-ethyl chloride;

formyl-dibenzyl-glycolic acid β-piperidinoethyl ester by the reaction of β-piperidino-ethyl chloride with formyl-dibenzyl-glycolic acid.

The following pharmacological investigations demonstrate the effectiveness of the compounds according to the present invention:

Pharmacological experiments

The anti-hypertensive action of acetyl-dibenzyl-glycolic acid β-piperidinoethyl ester hydrochloride (substance A) was demonstrated on awake rats by the following experiments:

The right kidneys of 42 male Wistar rats with weights of 100 g. were ligatured by the method described by Grollmann (Proc. Soc. Exp. Biol. Med., 57, 102–104/1944) for the production of chronic high pressure. 10 days afterwards, the left kidney was extirpated.

The measurement of the arterial blood pressure was carried out on the non-narcotised rats using the method of Friebel and Vreden (see Arch. Exp. Path. u. Pharmakol., 232, 419–422/1958), the blood pressure being meansured on the tails of the experimental animals. The pulse curves so obtained were recorded with the help of microphones and read off on oscillographs, whereas the blood pressure values were read off on a mercury manometer.

The blood pressure was measured twice weekly on Mondays and Thursdays, the average values $\bar{x}$ being calculated, with standard deviations, for each group.

If the arterial blood pressure of the animals, in the course of 4 to 6 weeks after the kidney extirpation, had reached or exceeded the value of 160 mm.Hg., then these animals were regarded as being hypertensive. Animals, the blood pressure of which had not increased correspondingly, were removed from the experiment.

From that time onwards, the test compounds and the control solutions were administered intragastrally, using a stomach tube.

There were administered:
1. to the control animals:
    1 ml. 0.9% sodium chloride solution intragastrally per 100 g. body weight.
2. to the experimental animals:
    100 mg./kg. substance A(B-N-piperidinoethyl O-acetyl-dibenzyl glycolate) intragastrally in 0.9% sodium chloride solution.

The concentration of substance A was so chosen that all the doses administered could be given, in each case, in 1 ml. physiological sodium chloride solution.

On the days on which the blood pressure of the animals was measured, the administration of the test compound or control solutions each took place 30 minutes before the pressure measurement on the individual animals.

Results

Substance A shows, even at a dosage of 75 mg./kg. intragastrally, a reproducible anit-hypertensive effect. The arterial blood pressure is, on average, already reduced by 20 –30 mm.Hg. 3 days after commencement of the treatment. In the course of 2 weeks, there is obtained a reduction of up to 60 mm.Hg. which, after discontinuation of the administration, does not begin to increase again until after 2 weeks. With an $LD_{50}$ of 821 mg./kg. in the case of intragastral administration, this compound gives good therapeutic quotient of 10.75. Most compounds used therapeutically for the treatment of high blood pressure, for example the Rauwolfia alkaloids, are administered together with diuretic-active materials, since the individual substances alone cannot reduce the blood pressure of renal hypertensive rats. In contradistinction thereto, substance A shows an extraordinary and longlasting anti-hypertensive effect.

The anti-secretory action of acetyl-dibenzyl-glycolic acid β-(2,2,6,6-tetramethylpiperidino)-ethyl ester (substance B) was demonstrated by the following experiments:

Investigations on rats, using Shay's experiment, gave a dosage-dependent inhibition of the gastric secretion after 15 mg./kg. i.g. (17%) with a practically complete (96%) inhibition of the secretion after 250 mg/kg. The pH displacement (pH 1.5 – pH 7) took place almost parallel in the given dosage range.

In the case of the Pavlov dog, 50 mg./kg. i.g. brought about, for at least one hour, an inhibition of the spontaneous secretion of 30 to 50% of the initial value, with a simultaneous pH increase up to a maximum of 100%. Side effects were not observed.

In the case of toxicity testing on mice, a slight side efect on the experimental animals was only observed after the intragastral administration of 1600 mg. substance B/kg. The toxicity is, therefore, very low.

We claim:

1. A method of treating hypertonia and hyperacidity in a mammal by the administration to said animal of an effective amount of a compound having the formula:

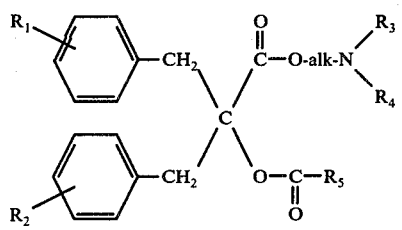

wherein $R_1$ and $R_2$, which may be the same or different, are hydrogen, halogen, or lower alkyl or lower alkoxy of 1 to 3 carbon atoms; $R_3$ and $R_4$, which may be the same or different, are lower alkyl of 1 to 3 carbon atoms or $R_3$ and $R_4$, together with the nitrogen atom to which they are attached, is a saturated or unsaturated ring structure of 3 to 5 carbon atoms which, in the ring system, can contain an oxygen or imino group and can be substituted by a phenyl or benzyl radical or by lower alkyls of 1 to 4 carbon atoms; $R_5$ is hydrogen, lower alkyl or alkoxyalkyl of 1 to 5 carbon atoms or benzyl; alk is a branched or unbranched alkylidene of 2 to 4 carbon atoms; and the quaternary lower alkyl ammonium halides thereof and the pharmaclogically compatible salts thereof.

2. The method according to claim 1 wherein the compound is of the formula:

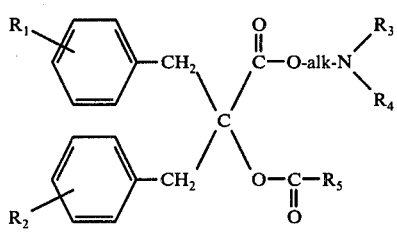

wherein $R_1$ and $R_2$ which may be the same or different are hydrogen, halogen, alkyl of up to 3 carbons, alkoxy of up to 3 carbons; wherein $R_3$ and $R_4$ which may be the same or different are alkyl of up to 3 carbons, or together with the nitrogen atom to which they are attached are azetidine, pyrrolidine, $\Delta^2$-pyrroline, $\Delta^3$-pyrroline, piperidine, piperazine, morpholine, tetrahydropyridine tetrahydroquinoline, tetrahydroisoquinoline, 2,2,6,6-bis-tetramethylenepyrrolindine, 2,2,6,6-bis-pentamethylenepyrrolidine, 4,4-tetramethylenepiperidine, 4,4-pentamethylenepiperidine, 4,4-hexamethylenepiperidine, hexahydroazepine, or 3-aza-bicyclo[3.2.2]nonane; and wherein $R_5$ is hydrogen, methyl, ethyl, n-propyl, isopropyl, n-butyl, isobutyl, t-butyl, methoxymethyl, or benzyl; wherein alk is alkylene of 2 to 4 carbon atoms; and the quaternary lower alkyl ammonium halides thereof and the pharmacological compatible salts thereof.

3. A method according to claim 2 wherein $R_1$ and $R_2$ are hydrogen, alk is ethyl and $R_5$ is methyl.

4. A method according to claim 3 wherein $R_3$ and $R_4$ together with the nitrogen atom to which they are attached is piperidino or a substituted piperidino wherein the substituent is a phenyl group or lower alkyl groups of 1 to 4 carbons.

5. A method of treating hypertonia and hyderacidity in a mammal by the administration to said animal of an effective amount of a compound having the formula:

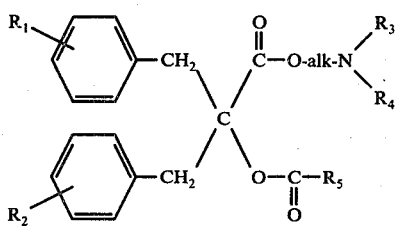

wherein $R_1$ and $R_2$ which may be the same or different are hydrogen, chlorine, methyl, or methoxy wherein $R_3$ and $R_4$ together with the nitrogen atom to which they are attached are piperidine, 2,2,6,6-tetramethylpiperidine, hexahydroazepine, or morpholine; wherein $R_5$ is methyl, ethyl or benzyl, wherein alk is ethylene; and the quaternary lower alkyl ammonium halides thereof and thepharmacologically compatible salts thereof.

6. A method according to claim 4 wherein $R_3$ and $R_4$ together with the nitrogen atom to which they are attached is monomethyl piperidino.

7. A method according to claim 4 wherein $R_3$ and $R_4$ together with the nitrogen atom to which they are attached is tetramethyl piperidino.

8. A method according to claim 4 wherein $R_3$ and $R_4$ together with the nitrogen atom to which they are attached is dimethyl piperidino.

9. A method according to claim 4 which is acetyl dibenzyl glycolic acid $\beta$-(2,2,6,6-tetraethylpiperidino)ethyl ester.

10. A method according to claim 3 wherein $R_3$ and $R_4$ are lower alkyls of 1 to 3 carbon atoms.

11. A method according to claim 3 wherein $R_3$ and $R_4$ together with the nitrogen atom to which they are attached belong to the group consisting of pyrrolidino, 2,2,5,5-tetramethylpyrrolidino, and 2,2,5,5-tetramethyl-$\Delta^{3,4}$-pyrrolidino.

12. A method according to claim 3 wherein $R_3$ and $R_4$ together with the nitrogen atom to which they are attached belong to the group consisting of 4,4-pentamethylene piperidino, 2,2,4,4-bis-tetramethylene piperidino, 2,2,4,4-bis-pentamethylene piperidino, 4,4-tetramethylene piperidino, and 4,4-hexamethylene piperidino.

13. A method according to claim 3 wherein $R_3$ and $R_4$ together with the nitrogen atom to which they are attached belong to the group consisting of morpholino, 1,2,5,6-tetrahydro-$\gamma$-picalylo, 1,2,3,4-tetrahydroquinolino, and 2,2,4,4-tetramethylazetidino.

14. A method according to claim 3 which is acetyldibenzyl glycolic acid-$\beta$-hexamethyleneimino-ethyl ester or its methobromide salt.

15. A method according to claim 3 which is acetal dibenzo glycolic acid $\beta$-(3-aza-bicyclo-[3.2.2]nonano)-ethyl ester.

16. A method according to claim 3 wherein $R_3$ and $R_4$ together with the nitrogen atom to which they are attached belong to the group consisting of 4-methyl piperizino-1,4-benzylpiperixino-1, and 4-phenylpiperizino-1.

17. A method according to claim 2 wherein $R_1$ and $R_2$ are hydrogen, $R_5$ is methyl and alk is propyl or isopropyl.

18. A method according to claim 17 wherein both $R_3$ and $R_4$ are methyl or ethyl.

19. A method according to claim 17 wherein $R_3$ and $R_4$ together with the nitrogen atom to which they are attached is piperidino.

20. A method according to claim 2 wherein $R_1$ and $R_2$ are hydrogen, $R_5$ is ethyl, alk is ethyl or porpyl and $R_3$ and $R_4$ are methyl or ethyl.

21. A method according to claim 2 wherein $R_1$ and $R_2$ are hydrogen, $R_5$ is ethyl, alk is ethyl and $R_3$ and $R_4$ together with the nitrogen atom to which they are attached are selected from the group consisting of pyrrolidino, piperidino, and morpholino.

22. A method according to claim 2 wherein $R_1$ and $R_2$ are hydrogen, alk is ethyl, $R_3$ and $R_4$ together with the nitrogen atom to which they are attached is piperidino and $R_5$ is a radical selected from the group consisting of isobutyryl, pivalolyl, methoxyacetyl, phenylacetyl, and formyl.

23. A method according to claim 2 wherein $R_1$ and $R_2$ are chlorine, $R_3$ and $R_4$ together with the nitrogen atom to which they are attached are piperidinoethyl, 2,2,6,6-tetramethylpiperidino, or hexamethyleneimino, alk is ethyl, and $R_5$ is methyl.

24. A method according to claim 2 wherein $R_1$ and $R_2$ are methyl, $R_3$ and $R_4$ together with the nitrogen atom to which they are attached are from the group consisting of piperidinoethyl and 2,2,6,6-tetramethylpiperidino, $R_5$ is methyl and alk is ethyl.

25. A method according to claim 2 wherein $R_1$ and $R_2$ are methoxy, $R_3$ and $R_4$ together with the nitrogen atom to which they are attached are piperidino or 2,2,6,6-tetramethylpiperidino, $R_5$ is methyl and alk is ethyl.

26. A method of treating hypertonia and hyperacidity in a mammal by the administration to said animal of an effective amount of an acetyl-dibenzylglycolic acid-$\beta$-R-ester wherein R is selected from the group consisting of:
piperidinoethyl,
2,2,6,6-tetramethyl-piperidino-ethyl,
dimethylaminoethyl,
diethylaminoethyl,
dimethylaminopropyl,
pyrrolidinoethyl,
morpholinoethyl,
piperidino-isopropyl,
piperidinopropyl,
(2-methyl-piperidino)-ethyl,
(3-methyl-piperidino)-ethyl,
(4-methyl-piperidino)-ethyl,
(2,6-dimethylpiperidino)-ethyl,
(4-phenyl-piperidino)-ethyl,
(4,4-pentamethylene-piperidino)-ethyl, and
hexamethyleneiminoethyl,
and pharmaceutically compatable quaternary lower alkyl ammonium halides and pharmaceutically compatible inorganic and organic acid salts thereof.

27. The method according to claim 26 which is acetyl-dibenzyl-glycolic acid -$\beta$-piperindinoethyl ester.

28. The method of claim 26 which is acetyl-dibenzyl-glycolic acid-$\beta$-2,2,6,6-tetreamethyl-piperidinoethyl ester.

29. The method of claim 26 which is acetyl-dibenzyl-glycolic acid-$\beta$-dimethylaminoethyl ester.

30. The method of claim 26 which is acetyl-dibenzyl-glycolic acid-$\beta$-diethylaminoethyl-ester.

31. A method of claim 26 wherein the compound is acetyl-dibenzylglycolic acid-$\beta$-dimethylaminopropyl-ester.

32. A method of claim 26 wherein the compound is acetyl-dibenzylglycolic acid-$\beta$-pyrrolidinoethyl ester.

33. A method of claim 26 wherein the compound is acetyl-dibenzylglycolic acid-$\beta$-morpholinoethyl ester.

34. A method of claim 26 wherein the compound is acetyl-dibenzylglycolic acid-$\beta$-piperidino-isopropyl ester.

35. A method of claim 26 wherein the compound is acetyl-dibenzylglycolic acid-$\beta$-piperidinopropyl ester.

36. A method of claim 26 wherein th compound is acetyl-dibenzylglycolic acid-$\beta$-(3-methyl-piperidino)ethyl ester.

37. A method of claim 26 wherein R is:
(2-methyl-piperidino)-ethyl,
(4-methyl-piperidino)-ethyl,
(2,6-dimethylpiperidino)-ethyl,
(4-phenyl-piperidino)-ethyl,
(4,4-pentamethylene-piperidino)-ethyl, and
hexamethyleneiminoethyl.

38. A method of claim 37 wherein the compound is acetyl-dibenzylglycolic acid-$\beta$-(2-methyl-piperidino)-ethyl ester.

39. A method of claim 37 wherein the compound is acetyl-dibenzylglycolic acid-$\beta$-(4-methyl-piperidino)-ethyl ester.

40. A method of claim 37 wherein the compound is acetyl-dibenzylglycolic acid-$\beta$-(2,6-dimethyl-piperidino)-ethyl ester.

41. A method of claim 37 wherein the compound is acetyl-dibenzyl-glycolic acid $\beta$-(4-phenyl-piperidino)-ethyl ester.

42. A method of claim 37 wherein the compound is acetyl-dibenzylglycolic acid-$\beta$-(4,4-pentamethylene-piperidino)-ethyl ester.

43. A method of claim 37 wherein the compound is acetyl-dibenzylglycolic acid-$\beta$-hexamethyleneimino-ethyl ester.

* * * * *